United States Patent
Cooper et al.

(10) Patent No.: US 8,735,515 B2
(45) Date of Patent: May 27, 2014

(54) "GREEN" PLASTIC MATERIALS AND METHODS OF MANUFACTURING THE SAME

(75) Inventors: Scott Cooper, Humble, TX (US); Olga Khabashesku, Houston, TX (US)

(73) Assignee: Fina Technology, Inc., Houston, TX (US)

( * ) Notice: Subject to any disclaimer, the term of this patent is extended or adjusted under 35 U.S.C. 154(b) by 85 days.

(21) Appl. No.: 13/191,524

(22) Filed: Jul. 27, 2011

(65) Prior Publication Data

US 2012/0046427 A1 Feb. 23, 2012

Related U.S. Application Data

(60) Provisional application No. 61/375,133, filed on Aug. 19, 2010.

(51) Int. Cl.
*C08F 2/00* (2006.01)
*C08G 63/127* (2006.01)
*C07C 2/00* (2006.01)

(52) U.S. Cl.
USPC .......... 526/75; 526/346; 527/100; 528/308.3; 585/240; 585/322; 585/323; 585/408

(58) Field of Classification Search
USPC ............. 526/75, 346; 528/308.1, 308.3; 585/240, 322, 323, 408; 527/100
See application file for complete search history.

(56) References Cited

U.S. PATENT DOCUMENTS

| | | | | |
|---|---|---|---|---|
| 4,400,569 A * | 8/1983 | Hunton | ........................ | 585/444 |
| 6,358,717 B1 * | 3/2002 | Blaschek et al. | ............. | 435/160 |
| 8,053,615 B2 * | 11/2011 | Cortright et al. | ............. | 585/240 |
| 2009/0246430 A1 * | 10/2009 | Kriegel et al. | ............. | 428/36.6 |
| 2009/0299109 A1 | 12/2009 | Gruber et al. | | |
| 2010/0041931 A1 | 2/2010 | Pelati et al. | | |
| 2010/0168371 A1 * | 7/2010 | Berti et al. | ............. | 528/308.1 |
| 2010/0205863 A1 | 8/2010 | Biollaz et al. | | |

FOREIGN PATENT DOCUMENTS

| | | |
|---|---|---|
| WO | 8500164 A1 | 1/1985 |
| WO | 2010078328 A2 | 7/2010 |

* cited by examiner

*Primary Examiner* — Fred M Teskin

(57) ABSTRACT

A process is disclosed for producing plastic materials by providing a biology based feedstock and reacting the biology based feedstock to form a feedstock capable of reaction to form the plastic material, wherein the plastic material is selected from polystyrene and polyethylene terephthalate (PET).

4 Claims, 1 Drawing Sheet

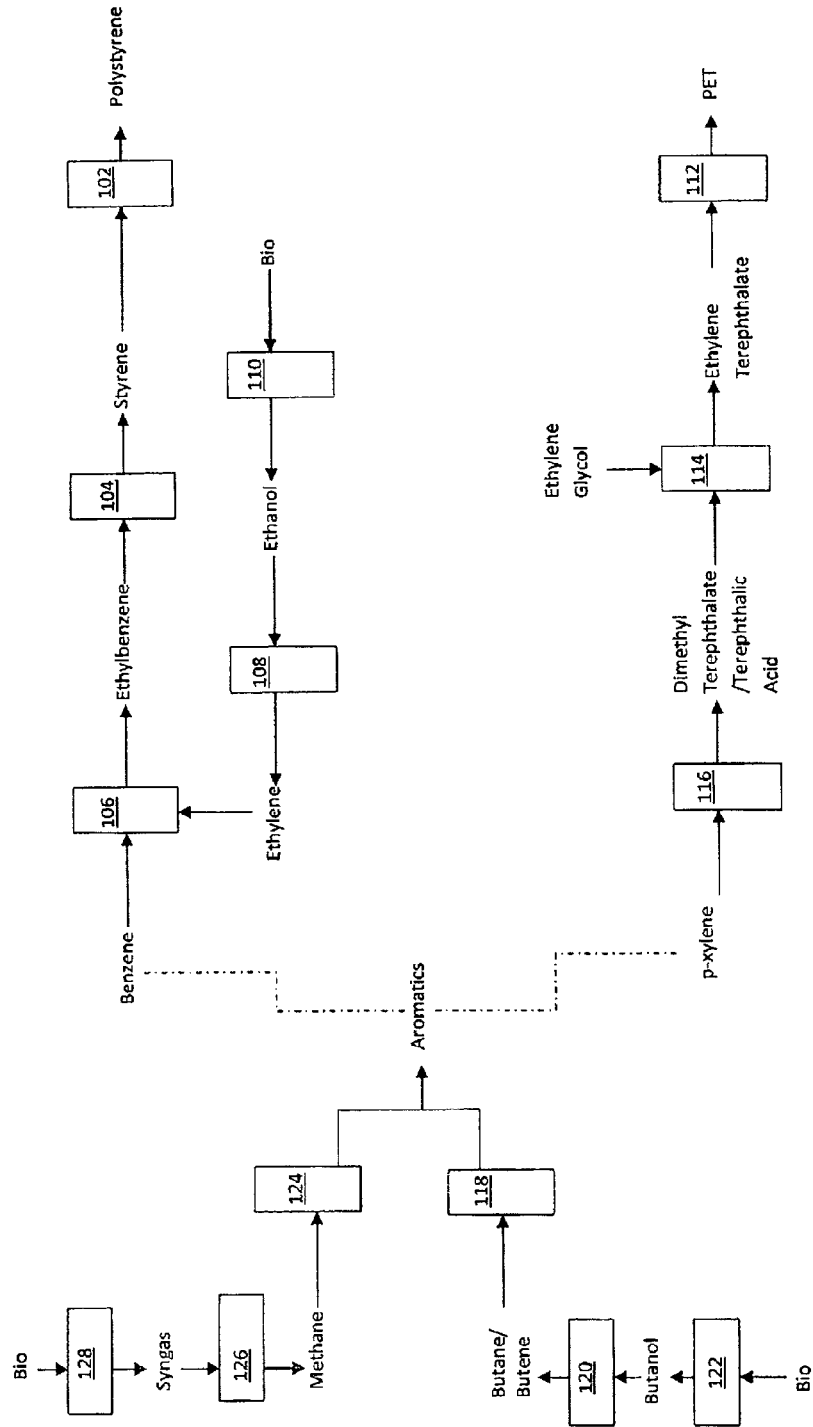

"GREEN" PLASTIC MATERIALS AND METHODS OF MANUFACTURING THE SAME

FIELD

Embodiments of the present invention generally relate to plastic materials formed from green technologies.

BACKGROUND

Today, 200 billion pounds (100 million tons) of plastics are produced worldwide every year. Plastics are used for packaging, building materials, and virtually every type of consumer product. Virtually all plastics are made from nonrenewable resources, such as oil, coal or natural gas, which will eventually become exhausted. Accordingly, plastics are the focus of an emerging industry focused on making convenient living consistent with environmental stability. One reason to make a shift toward the use of green plastics is the availability of raw materials. Another favorable property of some green plastics is their biodegradability, making them a natural material for use in such applications as compostable collection bags, such as for food or yard waste.

However, bioplastics have to possess adequate physical properties. Their properties have to be managed and controlled with technological means through the development of adequate formulations and plastics processing. Furthermore, bioplastics also have to be cost-competitive. Commercially available biopolymers are typically more expensive than synthetic polymers, often significantly so.

Therefore, a need exists to develop technologies to form plastic materials from green technologies.

SUMMARY

Embodiments of the present disclosure include processes for the production of plastic materials that are produced from a biology-based feedstocks.

In one embodiment of the present disclosure, a process of producing plastic materials that comprises providing a biology based feedstock; reacting the biology based feedstock to form a feedstock capable of reaction to form the plastic material, wherein the plastic material is selected from polystyrene and polyethylene terephthalate (PET), is disclosed.

In another embodiment of the present disclosure, either by itself or in combination with any other embodiment, a plastic material formed by the process wherein a biology based feedstock is used, is disclosed. The plastic material may be formed entirely of feedstocks formed from biology based feedstocks.

In another embodiment of the present disclosure, either by itself or in combination with any other embodiment, the plastic material may be polystyrene. In another embodiment of the present disclosure, either by itself or in combination with any other embodiment, the feedstock may comprise syngas. In another embodiment of the present disclosure, either by itself or in combination with any other embodiment, the process may further comprise alkylation of benzene derived from the feedstock and ethylene derived from a biology based material. In another embodiment of the present disclosure, either by itself or in combination with any other embodiment, the process may further comprise aromatization of methane formed from the sygas to form benzene.

In another embodiment of the present disclosure, either by itself or in combination with any other embodiment, the plastic material may be polyethylene terephthalate (PET). In another embodiment of the present disclosure, either by itself or in combination with any other embodiment, the feedstock may comprise butanol. In another embodiment of the present disclosure, either by itself or in combination with any other embodiment, the process may further comprise aromatization of butane, butene or combinations thereof formed from the dehydration of bio-butanol to form p-xylene.

The various embodiments of the present disclosure can be joined in combination with other embodiments and the listed embodiments herein are not meant to be limiting. All combinations of embodiments are enabled, even if not given in a particular example herein.

BRIEF DESCRIPTION OF DRAWINGS

The drawing illustrates an overall process schematic to form plastic materials.

DETAILED DESCRIPTION

Introduction and Definitions

A detailed description will now be provided. Each of the appended claims defines a separate invention, which for infringement purposes is recognized as including equivalents to the various elements or limitations specified in the claims. Depending on the context, all references below to the "invention" may in some cases refer to certain specific embodiments only. In other cases it will be recognized that references to the "invention" will refer to subject matter recited in one or more, but not necessarily all, of the claims. Each of the inventions will now be described in greater detail below, including specific embodiments, versions and examples, but the inventions are not limited to these embodiments, versions or examples, which are included to enable a person having ordinary skill in the art to make and use the inventions when the information in this patent is combined with available information and technology.

Various terms as used herein are shown below. To the extent a term used in a claim is not defined below, it should be given the broadest definition skilled persons in the pertinent art have given that term as reflected in printed publications and issued patents at the time of filing. Further, unless otherwise specified, all compounds described herein may be substituted or unsubstituted and the listing of compounds includes derivatives thereof.

Further, various ranges and/or numerical limitations may be expressly stated below. It should be recognized that unless stated otherwise, it is intended that endpoints are to be interchangeable. Further, any ranges include iterative ranges of like magnitude falling within the expressly stated ranges or limitations.

Embodiments of the invention generally include forming plastic materials from green technologies. Such green technologies are capable of reducing the carbon footprint of plastics production (providing for the reuse of carbonaceous materials). While it is recognized that the plastic materials are not strictly green products since they are not necessarily biodegradable, for the purposes described herein, since the feed is renewable, it shall be referred to as "green".

In one or more embodiments the plastic material is polystyrene. Polystyrene is a versatile polymer with a broad range of applications. For example, polystyrene may be used in packaging applications, electronics, appliances, computer housings, CD cases, kitchen, laboratory, office and medical goods and in building and construction. In another embodiment, the bio-sourced plastic material is polyethylene terephthalate (PET). PET may be used to produce a variety of products, such as filament and staple fiber, film, tire cord, technical yarns, plastic bottles and packaging resins, for example.

The polystyrene may be formed by known methods, such as free radical initiation of styrene or ioinc and metal catalyzed polymerization, for example. Such polymerization processes may include suspension, solution or bulk polymerization processes, for example. Such processes generally form general-purpose or high-impact polystyrene or expanded polystyrene, for example. The production of general-purpose and high-impact polystyrenes is generally similar with the exception of an initial rubber-dissolution step for high-impact polystyrene. The production of high-impact polystyrene may begin with granulation, or grinding, and dissolution of rubber and other additives in styrene monomer and then transfer of the rubber solution to storage tanks, for example. From this point on, the production steps for general-purpose polystyrene and high-impact polystyrene are essentially the same. The feed mixture may be preheated and fed continuously to a prepolymerizer. Prepolymerization may be initiated thermally or chemically depending on the product desired, for example.

Following prepolymerization, the polymer mixture may be pumped through a polymerization reactor system. The formed polymer mixture may then be preheated in preparation for devolatilization, which includes subjecting the formed polymer mixture to vacuum to remove unreacted monomer and solvent from the polymer melt.

Styrene is most commonly produced by the catalytic dehydrogenation of ethylbenzene. Such dehydrogenation processes generally include contacting ethylbenzene with steam and superheating the mixture prior to dehydrogenation in the presence of a dehydrogenation catalyst, such as iron(III) oxide catalysts, for example. The dehydrogenation catalysts may be promoted with known promoters, such as potassium oxide or potassium carbonate, for example.

Ethylbenzene is an organic compound with the formula $C_6H_5CH_2CH_3$. Although often present in small amounts in crude oil, ethylbenzene is generally produced in bulk quantities by liquid or vapor phase alkylation of benzene with ethylene in the presence of an alkylation catalyst. Such alkylation processes generally utilize zeolite catalysts, however, Friedel-Crafts catalyst are also contemplated for use herein.

Ethylene is generally produced from thermal cracking of hydrocarbon feedstocks derived from natural gas and crude oil. However, embodiments of the invention utilize green technologies to form the ethylene that is subsequently utilized to form the plastic materials. For example, the ethylene can be derived from ethanol. The conversion of ethanol to ethylene may include processes, such as catalytic dehydration via the following chemical reaction:

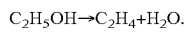

$$C_2H_5OH \rightarrow C_2H_4 + H_2O.$$

The ethanol, in one or more embodiments, may be formed from green technologies, such as via fermentation, for example. Ethanol fermentation, also referred to as alcoholic fermentation, is a biological process in which sugars, such as glucose, fructose, and sucrose are converted into cellular energy and thereby produce ethanol and carbon dioxide as metabolic waste products. Because yeasts perform this process in the absence of oxygen, ethanol fermentation is classified as anaerobic. The sugars are generally are generally bio-based materials, described in further detail regarding syngas below.

As mentioned previously herein, the plastic material includes polyethylene terephthalate (PET) in an alternative embodiment. PET is formed of polymerized units of the monomer ethylene terephthalate with repeating $C_{10}H_8O_4$ units. Polymerization may be through a polycondensation reaction of the monomers (done immediately after esterification/transesterification) with ethylene glycol as byproduct (the ethylene glycol may be directly recycled in production), for example. Its monomer (bis-β-hydroxyterephthalate) can be synthesized by the esterification reaction between terephthalic acid and ethylene glycol with water as a byproduct, or by transesterification reaction between ethylene glycol and dimethyl terephthalate with methanol as a byproduct, for example.

Terephthalic acid may be produced by oxidation of paraxylene (p-xylene) by oxygen in air, for example. The oxidation may be conducted using acetic acid as solvent and a catalyst, such as a catalyst including cobalt and manganese salts, for example. The catalyst may further include a promoter, such as bromide, for example. The solution may then be cooled in a stepwise manner to crystallize highly pure terephthalic acid. Alternatively, the terephthalic acid may be formed by the so-called "Henkel process". This process involves the rearrangement of phthalic acid to terephthalic acid via the corresponding potassium salts.

The term xylene or xylol refers to a mixture of three aromatic hydrocarbon isomers closely related to benzene. Xylene is a clear, colorless, sweet-smelling liquid that is very flammable and encompasses ortho-, meta-, and para-isomers of dimethyl benzene. The o-, m- and p-designations specify to which carbon atoms (of the benzene ring) the two methyl groups are attached. Counting the carbon atoms from one of the ring carbons bonded to a methyl group, and counting towards the second ring carbon bonded to a methyl group, the o-isomer has the IUPAC name of 1,2-dimethylbenzene, the m-isomer has the IUPAC name of 1,3-dimethylbenzene, and the p-isomer has the IUPAC name of 1,4-dimethylbenzene.

Historically, aromatic hydrocarbons (e.g., benzene and xylenes) have been formed by one of four chemical processes: catalytic reforming, toluene hydrodealkylation, toluene disproportionation and steam cracking. In traditional catalytic reforming, a mixture of hydrocarbons with boiling points between 60° C. to 200° C. is blended with hydrogen gas and then exposed to a reforming catalyst to form ring structures and lose hydrogen to become aromatic hydrocarbons.

However, embodiments of the invention utilize green technologies to form the aromatic hydrocarbons that are subsequently utilized to form the plastic materials. For example, in one or more embodiments, the aromatic compounds are formed from "green" paraffins (i.e., alkanes), such as methane or butane.

Alkanes may be converted into aromatic hydrocarbons via catalytic aromatization (which includes dehydrogenation, oligomerization, and aromatization), for example. Dehydrogenation converts the alkane feedstock into olefins and generally occurs via one of two reactions; either a hydrogen-carbon bond on an alkane is broken to form a hydrogen atom and the corresponding olefin or carbon-carbon bond fissure takes place to form a lighter alkane and an olefin. Alkene interconversion includes alkene isomerization, oligomerization and cracking to form cyclic napthenes. Aromatization includes dehydrogenation of the cyclic napthenes to their corresponding aromatic hydrocarbons in a sequence of cyclization and hydrogen transfer steps.

In one or more specific embodiments, the paraffin is "green" methane formed from "green" syngas. Syngas is a gas mixture containing varying amounts of carbon monoxide (CO), hydrogen and often, carbon dioxide ($CO_2$). Conventional methods of forming syngas include steam reforming of natural gas or liquid hydrocarbons and gasification of coal or biomass, for example. However, embodiments of the invention utilize green technologies to form the syngas for subsequent plastics production processes.

In one or more embodiments, the syngas is formed from plasma pyrolysis of carbon containing biology-based (bio-based) materials. In one or more embodiments, the bio-based material is derived from biomass, such as lignin, corn, sugar cane, syrup, beet juice, molasses, cellulose, sorbitol, algae, glucose, duckweed, pearl millet, sorghum, rice, grapes, acetates, such as ethyl acetate or methyl acetate or combinations thereof. As used herein, the term "biomass" excludes organic material which has been transformed by geological processes into substances, such as petroleum. In one or more embodiments, the bio-based material is derived from biogas, such as that produced by anaerobic digestion or fermentation of biodegradable materials, including biomass, manure, sewage, energy crops or combinations thereof, for example. As used herein, the term "biogas" refers to a gas produced by the biological breakdown of organic matter in the absence of oxygen.

In one or more specific embodiments, the bio-based material includes waste materials, such as municipal solid waste. Utilization of waste materials reduces the volume of waste entering landfills.

Syngas (or components thereof) may be formed from waste materials (identified as "C") as shown in the non-limiting reaction schemes illustrated below:

$$C+H_2O \rightarrow CO+H_2;$$

$$C+O_2 \rightarrow CO_2; \text{ and}$$

$$CO_2+C \rightarrow 2CO.$$

Plasma pyrolysis generally includes gasification of a waste material, either in a furnace or reactor, with a plasma arc torch. The plasma arc torch may utilize gas, air or steam and powerful electrodes to form plasma (i.e., an ionized gas). Plasma pyrolysis generally utilizes temperatures as high as 10,000° F. to break molecular bonds through dissociation, creating basic atoms. Further, such high temperatures provide fusion of non-flammable inorganic components and their transformation to slag and metal components, which may be subsequently separated from the plasma through known technologies, such as floating separation, for example.

Use of plasma torches provides advantages over incinerators or other combustion processes because the intense heat generated by the plasma torch dissociates the waste material, causing the organic components of the waste to be turned to gas and causing the inorganic components of the waste to be converted to a relatively small volume of inert vitrified material without combustion or incineration. The gaseous stream consists primarily of hydrogen and carbon monoxide, the primary combustible components of syngas.

Occasionally, plasma pyrolysis includes the introduction of oxygen, which further promotes the formation of CO and $CO_2$. However, in processes utilizing little to no additional oxygen, the formed gas may include methane ($CH_4$), which may then be used directly in aromatics production processes, discussed above.

In another embodiment, the aromatic compounds are formed from "green" butane/butene. The "green" butane/butene may be formed from dehydrogenation of butanol. The butanol may be formed by "green" technologies, such as fermenting a bio-based material, such as those discussed above, or gasification of biomass, for example.

In utilizing the processes described herein, plastic materials are formed, which may be formed from a significant amount of organic material. As illustrated in the drawing (showing a summary schematic of an embodiment), one or more embodiments are capable of forming materials from 100% organic materials.

The drawing illustrates an overall process schematic to form plastic materials, such as polystyrene and/or PET. As discussed above, the polystyrene may be formed by polymerization (102) of styrene. The styrene may be formed by dehydrogenation (104) of ethylbenzene. The ethylbenzene may be formed by the alkylation (106) of benzene with ethylene. The ethylene may be formed by the dehydration (108) of ethanol. The ethanol may be formed by the fermentation (110) of a bio-based material.

The PET may be formed by the polymerization (112) of ethylene terephthalate. The ethylene terephthalate may be formed by the esterification (114) of terephthalic acid. The terephthalic acid may be formed by the oxidation (116) of p-xylene.

The p-xylene may be formed by aromatization (118) of butane/butene, which may be formed by the dehydration (120) of butanol. The butanol may be formed by the fermentation (122) of a bio-based material. The benzene may be formed by aromatization (124) of methane, which may be formed by catalytic conversion (126) of syngas. The syngas may be formed by plasma pyrolysis (128) of a bio-based material.

While the foregoing is directed to embodiments of the present invention, other and further embodiments of the invention may be devised without departing from the basic scope thereof and the scope thereof is determined by the claims that follow.

What is claimed is:

1. A process of producing plastic materials comprising:
   providing a biology based feedstock;
   reacting the biology based feedstock to form a feedstock capable of reaction to form the plastic material, wherein the plastic material is polystyrene; and
   alkylation of benzene derived from the feedstock and ethylene derived from a biology based material.

2. The process of claim 1, wherein the feedstock comprises syngas.

3. A process of producing plastic materials comprising:
   providing a biology based feedstock;
   reacting the biology based feedstock to form a feedstock capable of reaction to form the plastic material, wherein the plastic material is polystyrene;
   wherein the feedstock comprises syngas; and
   aromatization of methane formed from the syngas to form benzene.

4. A process of producing plastic materials comprising:
   providing a biology based feedstock;
   reacting the biology based feedstock to form a feedstock capable of reaction to form the plastic material, wherein the plastic material is polyethylene terephthalate (PET), wherein the feedstock comprises butanol; and
   aromatization of butane, butene or combinations thereof formed from dehydration of bio-butanol to form p-xylene.

* * * * *